US006200776B1

(12) United States Patent
Boron et al.

(10) Patent No.: US 6,200,776 B1
(45) Date of Patent: Mar. 13, 2001

(54) POLYNUCLEOTIDES ENCODING HUMAN SODIUM BICARBONATE COTRANSPORTERS

(75) Inventors: Walter F Boron, Orange, CT (US); Antoine Michel Alain Bril, Saint-Gregoire (FR); Nassirah Khandoudi, Rennes (FR); Xavier Martin, Pace (FR); Steven Charles Jupe, Epping (GB); Christopher John Rawlings, Kings Langley (GB); Trudy Rachel Doe, Ware (GB)

(73) Assignees: Yale University School of Medicine, New Haven, CT (US); SmithKline Beecham Corporation P.L.C. (GB); SmithKline Beecham Laboratoires Pharmaceutiques, Nanterre Cedex (FR)

( * ) Notice: Subject to any disclaimer, the term of this patent is extended or adjusted under 35 U.S.C. 154(b) by 0 days.

(21) Appl. No.: 09/115,954

(22) Filed: Jul. 15, 1998

(30) Foreign Application Priority Data

Jul. 16, 1997 (EP) .................................. 97401713
Jul. 16, 1997 (EP) .................................. 97401714
Feb. 9, 1998 (EP) .................................. 98400272
Feb. 26, 1998 (EP) .................................. 98400454

(51) Int. Cl.[7] .............................. C12P 21/06; C12N 1/20; C12N 15/00; G01N 33/00; C07H 21/02
(52) U.S. Cl. .................. 435/69.1; 435/320.1; 435/252.3; 435/6; 436/94; 536/23.1
(58) Field of Search ........................ 536/23.1; 435/320.1, 435/252.31, 69.1, 6; 439/94

(56) References Cited

PUBLICATIONS

Grichtchenko et al. GenBank110 Database. Accession No. AF069512. Homo sapiens sodium bicarbonate cotransporter (NBC) mRNA, complete cds, Dec. 1998.*

Watson et al. Molecular Biology of the Gene, 4th edition. Inside cover, 1987.*

GenBank Accession # AF007216 Homosapiens sodium bicarbonate cotransporter (HNBC1) mRNA, complete cds.

GenBank Accession # AF001958 Ambystrone tigrinum electrogenic Na+bicarbonate cotransporter (NBC) mRNA, complete cds.

GenBank Accession # AF027362 Rathus narvegicus sodium bicarbonate cotransporter (rNBC1) mRNA, complete cds.

Burnham, C.F. et al., "Cloning and Functional Expression of a Human Kidney $Na^+:HCO_3$ Cotransporter", J. Biol. Chem., vol. 272 (31), pp. 19111–19114 (1997).

Romero et al., "Expression cloning and characterization of a renal electrogenic $Na^+/HCO^-_3$ cotransporter" Nature vol. 387, pp. 409–413 (1997).

Boron et al., "The Renal Electrogenic $Na^+:HCO_3^-$ Cotransporter", Journal of Experimental Biology, vol. 200, pp. 263–268 (1997).

Romero et al., "Cloning and Functional Expression of the Rat Renal Electrogenic Na/HCO3 Cotransporter" Journal of the American Society of Nephrology, vol. 7 (9) p. 1259 (1996).

* cited by examiner

Primary Examiner—Karen Cochrane Carlson
Assistant Examiner—Devesh Srivastava
(74) Attorney, Agent, or Firm—William T. Han; Ratner & Prestia; William T. King

(57) ABSTRACT

The hNBC3 polypeptides and polynucleotides and methods for producing such polypeptides by recombinant techniques are disclosed. Also disclosed are methods for utilizing hNBC3 polypeptides and polynucleotides in therapy, and diagnostic assays for such.

20 Claims, No Drawings

POLYNUCLEOTIDES ENCODING HUMAN SODIUM BICARBONATE COTRANSPORTERS

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach as a means to identifying genes and gene products as therapeutic targets is rapidly superceding earlier approaches based on 'positional cloning'. A phenotype, that is a biological function or genetic disease, would be identified and this would then be tracked back to the responsible gene, based on its genetic map position.

Functional genomics relies heavily on high throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to hNBC3, in particular hNBC3 polypeptides and hNBC3 polynucleotides, recombinant materials and methods for their production. In another aspect, the invention relates to methods for using such polypeptides and polynucleotides, including the treatment of ischaemic heart disease, arrhythmias, congestive heart disease, stroke and renal ischaemia, hereinafter referred to as "the Diseases", amongst others In a further aspect, the invention relates to methods for identifying agonists and antagonists/inhibitors using the materials provided by the invention, and treating conditions associated with hNBC3 imbalance with the identified compounds. In a still further aspect, the invention relates to diagnostic assays for detecting diseases associated with inappropriate hNBC3 activity or levels.

DESCRIPTION OF THE INVENTION

In a first aspect, the present invention relates to hNBC3 polypeptides. Such peptides include isolated polypetides comprising an amino acid sequence which has at least 70% identity, preferably at least 80% identity, more preferably at least 90% identity, yet more preferably at least 95% identity, most preferably at least 97–99% identity, to that of SEQ ID NO:2 over the entire length of SEQ ID NO:2. Such polypeptides include those comprising the amino acid sequence of SEQ ID NO:2. Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypep- tides include the polypeptide of SEQ ID NO:2. Further peptides of the present invention include isolated polypep- tides encoded by a polynucleotide comprising the sequence contained in SEQ ID NO:1.

In a further aspect, the present invention relates to hNBC3a polypeptides. An hNBCa polypeptide is an alternative form of hNBC which differs in sequence at the N-terminal end of the polypeptide. Such polypeptides may result from alternative splicing of the pre-mRNA transcribed from the hNBC3 gene. The polypeptides of SEQ ID NO:2 (hNBC3) and SEQ ID NO:8 (hNBC3a) are identical from amino acid position 44 (SEQ ID NO:2) and position 32 (SEQ ID NO:8) to the C-terminal end of the respective polypeptides. The difference in the N-terminal sequences arises as a result of an additional 19bp that are present in the polynucleotide encoding hNBC3a, SEQ ID NO:7. In order to translate the hNBC3a polypeptide an alternative start codon is required This alternative start codon may be found at nucleotide position 8–10 in SEQ ID NO:7.

hNBC3a peptides include isolated polypeptides comprising an amino acid sequence which has at least 70% identity, preferably at least 80% identity, more preferably at least 90% identity, yet more preferably at least 95% identity, most preferably at least 97–99% identity, to that of SEQ ID NO:8 over the entire length of SEQ ID NO:8. Such polypeptides include those comprising the amino acid sequence of SEQ ID NO:8. Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:8 over the entire length of SEQ ID NO:8. Such polypeptides include the polypeptide of SEQ ID NO:8. Further peptides of the present invention include isolated polypeptides encoded by a polynucleotide comprising the sequence contained in SEQ ID NO:7.

Polypeptides of the present invention are believed to be members of the sodium bicarbonate cotransporter family of polypeptides. They are therefore of interest because the Na+/HCO3-transporter (sodium-bicarbonate transporter ie. NBC), is one of the mechanisms involved in the regulation of intracellular pH. Acidosis established during myocardial ischemia stimulates NBC: extrusion of protons through NBC and is accompanied by cellular uptake of Na+, leading to more dangerous Ca2+ overload due to the functioning of Na+/Ca2+ exchanger in reverse-mode. This implies that specific inhibition of NBC will be of benefit in reduction of cellular injury during ischaemia. These properties of the hNBC3 and hNBC3a polypeptides are hereinafter referred to as "hNBC3 activity" or "hNBC3 polypeptide activity" or "biological activity of hNBC3". Also included amongst these activities are antigenic and immunogenic activities of said hNBC3 polypeptides, in particular the antigenic and immunogenic activities of the polypeptides of SEQ ID NO:2 or SEQ ID NO:8. Preferably, a polypeptide of the present invention exhibits at least one biological activity of hNBC3.

The polypeptides of the present invention may be in the form of the "mature" protein or may be a part of a larger protein such as a precursor or fusion protein. It is often advantageous to include an additional amino acid sequence which contains secretory or leader sequences, prosequences, sequences which aid in purification such as multiple histidine residues, or an additional sequence for stability during recombinant production.

The present invention also includes include variants of the aforementioned polypetides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to hNBC3 polynucleotides. The polynucleotide of SEQ ID NO:1 encodes the hNBC3 polypeptide and the polynucleotide of SEQ ID NO:7 encodes the hNBC3a polypeptide. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2 or SEQ ID NO:8, over the entire length of SEQ ID NO:2 or SEQ ID NO:8. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2 and a polynucleotide comprising the nucleotide sequence contained in SEQ ID NO:7 encoding the polypeptide of SEQ ID NO:8.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2 or SEQ ID NO:8, over the entire coding region. In this regard, polynucleotides which have at least 97% identity are highly preferred, whilst those with at least 98–99% identity are more highly preferred, and those with at least 99% identity are most highly preferred. Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 or SEQ ID NO:7 over the entire length of SEQ ID NO:1 or SEQ ID NO:7. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 or SEQ ID NO:7 as well as the polynucleotides of SEQ ID NO:1 and SEQ ID NO:7.

The invention also provides polynucleotides which are complementary to all the above described polynucleotides.

The nucleotide sequences of SEQ ID NO:1 and SEQ ID NO:7 show homology with human kidney Na+/HCO3- cotransporter (E. Burnham el al. J Biol Chem.272: 19111–19117, 1997). The nucleotide sequence of SEQ ID NO:1 is a cDNA sequence and encodes a polypeptide of SEQ ID NO:2 that has homology to Human kidney Na+/HCO3- cotransporter. The nucleotide sequence of SEQ ID NO:7 is a cDNA sequence and encodes a polypeptide of SEQ ID NO:8 that has homology to Human kidney Na+/HCO3- cotransporter. The nucleotide sequence encoding the polypeptide of SEQ ID NO:2 or SEQ ID NO:8 may be identical to the polypeptide encoding sequence contained in SEQ ID NO:1 or SEQ ID NO:7 or it may be a sequence other than the one contained in SEQ ID NO:1 or SEQ ID NO:7, which, as a result of the redundancy (degeneracy) of the genetic code, also encodes the polypeptide of SEQ ID NO:2 or SEQ ID NO:8. The polypeptides of SEQ ID NO:2 and SEQ ID NO:8 are structurally related to other proteins of the sodium bicarbonate cotransporter family, having homology and/or structural similarity with Human kidney Na+/HCO3- cotransporter (E. Burnham el al. J Biol Chem.272: 19111–19117, 1997).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one hNBC3 activity.

The present invention also relates to partial or other polynucleotide and polypeptide sequences which were first identified prior to the determination of the corresponding full length sequences of SEQ ID NO:1, SEQ ID NO:7, SEQ ID NO:2 and SEQ ID NO:8.

Accordingly, in a further aspect, the present invention provides for an isolated polynucleotide which:
(a) comprises a nucleotide sequence which has at least 70% identity, preferably at least 80% identity, more preferably at least 90% identity, yet more preferably at least 95% identity, even more preferably at least 97–99% identity to SEQ ID NO:3 over the entire length of SEQ ID NO:3;
(b) has a nucleotide sequence which has at least 70% identity, preferably at least 80% identity, more preferably at least 90% identity, yet more preferably at least 95% identity, even more preferably at least 97–99% identity, to SEQ ID NO:3 over the entire length of SEQ ID NO:3;
(c) the polynucleotide of SEQ ID NO:3; or
(d) a nucleotide sequence encoding a polypeptide which has at least 70% identity, preferably at least 80% identity, more preferably at least 90% identity, yet more preferably at least 95% identity, even more preferably at least 97–99% identity, to the amino acid sequence of SEQ ID NO:4, over the entire length of SEQ ID NO:4;
as well as the polynucleotide of SEQ ID NO:3.
(e) comprises a nucleotide sequence which has at least 70% identity, preferably at least 80% identity, more preferably at least 90% identity, yet more preferably at least 95% identity, even more preferably at least 97–99% identity to SEQ ID NO:5 or SEQ ID NO:9 over the entire length of SEQ ID NO:5 or SEQ ID NO9;
(f) has a nucleotide sequence which has at least 70% identity, preferably at least 80% identity, more preferably at least 90% identity, yet more preferably at least 95% identity, even more preferably at least 97–99% identity, to SEQ ID NO:5 or SEQ ID NO:9 over the entire length of SEQ ID NO:5 or SEQ ID NO:9;
(g) the polynucleotide of SEQ ID NO:5 or SEQ ID NO:9; or
(h) a nucleotide sequence encoding a polypeptide which has at least 70% identity, preferably at least 80% identity, more preferably at least 90% identity, yet more preferably at least 95% identity, even more preferably at least 97–99% identity, to the amino acid sequence of SEQ ID NO:6 or SEQ ID NO:10, over the entire length of SEQ ID NO:6 or SEQ ID NO:10;

as well as the polynucleotides of SEQ ID NO:5 and SEQ ID NO:9.

The present invention further provides for a polypeptide which:

(a) comprises an amino acid sequence which has at least 70% identity, preferably at least 80% identity, more preferably at least 90% identity, yet more preferably at least 95% identity, most preferably at least 97–99% identity, to that of SEQ ID NO:4 over the entire length of SEQ ID NO:4;

(b) has an amino acid sequence which is at least 70% identity, preferably at least 80% identity, more preferably at least 90% identity, yet more preferably at least 95% identity, most preferably at least 97–99% identity, to the amino acid sequence of SEQ ID NO:4 over the entire length of SEQ ID NO:4;

(c) comprises the amino acid of SEQ ID NO:4; and (d) is the polypeptide of SEQ ID NO:4;

as well as polypeptides encoded by a polynucleotide comprising the sequence contained in SEQ ID NO:3.

(e) comprises an amino acid sequence which has at least 70% identity, preferably at least 80% identity, more preferably at least 90% identity, yet more preferably at least 95% identity, most preferably at least 97–99% identity, to that of SEQ ID NO:6 or SEQ ID NO:10 over the entire length of SEQ ID NO:6 or SEQ ID NO:10;

(f) has an amino acid sequence which is at least 70% identity, preferably at least 80% identity, more preferably at least 90% identity, yet more preferably at least 95% identity, most preferably at least 97–99% identity, to the amino acid sequence of SEQ ID NO:6 or SEQ ID NO:10 over the entire length of SEQ ID NO:6 or SEQ ID NO:10;

(c) comprises the amino acid of SEQ ID NO:6 or SEQ ID NO:10; and (d) is the polypeptide of SEQ ID NO:6 or SEQ ID NO:10;

as well as polypeptides encoded by a polynucleotide comprising the sequence contained in SEQ ID NO:5 or SEQ ID NO:9.

The nucleotide sequences of SEQ ID NO:5 and SEQ ID NO:9 and the peptide sequence encoded thereby are derived from EST (Expressed Sequence Tag) sequences. It is recognised by those skilled in the art that there will inevitably be some nucleotide sequence reading errors in EST sequences (see Adams, M. D. et al, Nature 377 (supp) 3, 1995). Accordingly, the nucleotide sequences of SEQ ID NO:5 and SEQ ID NO:9 and the peptide sequence encoded therefrom are therefore subject to the same inherent limitations in sequence accuracy.

Polynucleotides of the present invention may be obtained, using standard cloning and screening techniques, from a cDNA library derived from mRNA in cells of human keratinocyte, thymus, leucocyte and brain, using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 or SEQ ID NO:8 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1 or SEQ ID NO:7, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1 or SEQ ID NO:7. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO:1 or SEQ ID NO:7 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stingent hybridization conditions with a labeled probe having the sequence of SEQ ID NO:1, SEQ ID NO:7 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, an ion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and or purification.

This invention also relates to the use of polynucleotides of the present invention as diagnostic reagents. Detection of a mutated form of the gene characterised by the polynucleotide of SEQ ID NO:1 or SEQ ID NO:7 which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled hNBC3 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al., *Science* (1985)230:1242). Sequence changes at specific locations may also be revealed by nuclease protection assays, such as RNase and S1 protection or the chemical cleavage method (see Cotton et al., *Proc Natl Acad Sci USA* (1985) 85: 4397–4401). In another embodiment, an array of oligonucleotides probes comprising hNBC3 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the hNBC3 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit which comprises:
(a) a polynucleotide of the present invention, preferably the nucleotide sequence of SEQ ID NO: 1, SEQ ID NO:7 or a fragment thereof;
(b) a nucleotide sequence complementary to that of (a);
(c) a polypeptide of the present invention, preferably the polypeptide of SEQ ID NO:2, SEQ ID NO:8 or a fragment thereof; or
(d) an antibody to a polypeptide of the present invention, preferably to the polypeptide of SEQ ID NO:2 or SEQ ID NO:8.

It will be appreciated that in any such kit, (a), (b), (c) or (d) may comprise a substantial component. Such a kit will be of use in diagnosing a disease or suspectability to a disease, particularly ischaemic heart disease, arrhythmias, congestive heart disease, stroke or renal ischaemia, amongst others.

The nucleotide sequences of the present invention are also valuable for chromosomal localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The nucleotide sequences of the present invention are also valuable for tissue localisation. Such techniques allow the determination of expression patterns of the hNBC3 polypeptides in tissues by detection of the mRNAs that encode them. These techniques include in situ hybridziation techniques and nucleotide amplification techniques, for example PCR.

Such techniques are well known in the art. Results from these studies provide an indication of the normal functions of the polypeptides in the organism. In addition, comparative studies of the normal expression pattern of hNBC3 mRNAs with that of mRNAs encoded by a mutant hNBC3 gene provide valuable insights into the role of mutant hNBC3 polypeptides, or that of inappropriate expression of normal hNBC3 polypeptides, in disease. Such inappropriate expression may be of a temporal, spatial or simply quantitative nature.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for one or more biological functions, including one or more disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., *Current Protocols in Immunology* 1 (2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring hNBC3 activity in the mixture, and comparing the hNBC3 activity of the mixture to a standard. Fusion proteins, such as those made from Fc portion and hNBC3 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening methods include those involving the measurement of changes in intracellular pH. Methods in which intracellular pH recovery after an intracellular acidification is recorded using specific fluorescent dye or microphysiometer method are particularly preferred.

The polynucleotides, polypeptides and antibodies to the polypeptide of the present invention may also be used to configure screening methods for detecting the effect of added compounds on the production of in RNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}I$), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypetide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;
(b) a recombinant cell expressing a polypeptide of the present invention;
(c) a cell membrane expressing a polypeptide of the present invention; or
(d) antibody to a polypeptide of the present invention;

which polypeptide is preferably that of SEQ ID NO:2 or SEQ ID NO:8.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:
(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors.

It will be further appreciated that this will normally be an iterative process.

In a further aspect, the present invention provides methods of treating abnormal conditions such as, for instance, ischaemic heart disease, arrhythmias, congestive heart disease, stroke or renal ischaemia, related to either an excess of, or an under-expression of, hNBC3 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the hNBC3 polypeptide.

In still another approach, expression of the gene encoding endogenous hNBC3 polypeptide can be inhibited using expression blocking techniques. Known such techniques involve the use of antisense sequences, either internally generated or externally administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the hNBC3 polypeptide may be prevented by using ribozymes specific to the hNBC3 mRNA sequence. Ribozymes are catalytically active RNAs that can be natural or synthetic (see for example Usman, N, et al., *Curr. Opin. Struct. Biol* (1996) 6(4), 527–33.) Synthetic ribozymes can be designed to specifically cleave hNBC3 mRNAs at selected positions thereby preventing translation of the hNBC3 mRNAs into functional polypeptide. Ribozymes may be synthesised with a natural ribose phosphate backbone and natural bases, as normally found in RNA molecules. Alternatively the ribosymes may be synthesised with non-natural backbones to provide protection from ribonuclease degradation, for example, 2'-O-methyl RNA, and may contain modified bases.

For treating abnormal conditions related to an under-expression of hNBC3 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of hNBC3 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in viva. For an overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as those in the GCG and Lasergene software packages. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the air. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques (see, e.g.: COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM *J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988)48:1073. Methods to determine identity and similarity are codified in computer programs. Preferred computer program methods to determine identity and similarity between two sequences include, but are not limited to, GCG program package (Devereux, J., et al., *Nucleic Acids Research* (1984) 12(1):387), BLASTP, BLASTN, and FASTA (Atschul, S. F. et al., *J Molec Biol* (1990) 215:403).

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity (divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described.

Falling within this generic term are the terms "ortholog", meaning a polynucleotide or polypeptide that is the functional equivalent of a polynucleotide or polypeptide in another species, and "paralog" meaning a functionally similar sequence when considered within the same species. Hence in the rat, for example, a member of the family of serotonin receptors is a paralog of the other members of the rat serotonin receptor family.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

SEQUENCE LISTING

<160> NUMBER OF SEQ ID NOS: 10

<210> SEQ ID NO 1
<211> LENGTH: 3912
<212> TYPE: DNA
<213> ORGANISM: Homo sapiens

<400> SEQUENCE: 1

| | | | | | | |
|---|---|---|---|---|---|---|
| ttggcttgga | gcccgtgggg | gagacctagt | tcggctccgc | catgccggcc | gccgggagta | 60 |
| acgagccgga | cggcgtcctc | agctatcaga | gaccagatga | agaagctgtg | gtggatcagg | 120 |
| gtgggaccag | tacaattctc | aacattcact | atgaaaaaga | agagctggaa | ggtcacagaa | 180 |
| ctctgtatgt | gggagttcgg | atgccgcttg | gccggcagag | ccatcggcat | caccgcactc | 240 |
| atggccagaa | gcaccggaga | cgagggcggg | gcaaaggagc | cagccagggg | gaggaaggcc | 300 |
| tggaagccct | ggcccacgac | acaccatctc | agcgtgttca | gttcattctt | ggcaccgagg | 360 |
| aagatgaaga | gcatgtgcct | catgagctgt | ttacagagct | ggatgagatc | tgtatgaaag | 420 |
| agggagaaga | tgctgagtgg | aaggaaacag | ccaggtggct | gaagtttgaa | gaagatgttg | 480 |
| aagatggggg | agaacgctgg | agcaagcctt | atgtggcaac | cctttcattg | cacagcctgt | 540 |
| ttgagctaag | gagctgcctt | attaatggaa | cagtcctcct | ggatatgcat | gcaaatagca | 600 |
| tagaagaaat | ttcagacctg | atcctggatc | agcaagaact | gtccagtgac | ctgaatgaca | 660 |
| gcatgagggt | taaagtgcgg | gaagcccttc | tcaaaaagca | tcatcatcag | aatgaaaaga | 720 |
| agagaaacaa | cctcattccc | attgttcgct | cctttgctga | ggttggcaag | aagcagtctg | 780 |
| atcctcattt | gatggataaa | catggtcaaa | ccgtgtctcc | tcagtctgtt | ccaactacaa | 840 |
| atcttgaagt | aaaaaatgga | gtgaattgtg | aacatagtcc | tgtggattta | agcaaggtag | 900 |
| accttcattt | catgaaaaaa | attcctactg | gggccgaggc | ctccaatgtc | ctggttggag | 960 |
| aggtggatat | tttggaccgt | cccattgttg | cctttgtgag | gctgtctcca | gctgttcttc | 1020 |
| tctcaggcct | aacagaagtg | ccaatcccaa | caagattttt | gtttatctta | ttgggtccag | 1080 |
| tagggaaagg | tcagcagtac | catgagattg | gcagatccat | ggccaccatc | atgacagatg | 1140 |
| agatttttca | tgacgtagca | tataaggcaa | agagcgaga | tgatctcctg | gcggggattg | 1200 |
| atgagttcct | agaccaggtg | acggtgctcc | ctccaggaga | gtgggatccc | tccattagaa | 1260 |
| ttgagccacc | caaaaatgtc | ccttcccagg | agaaaaggaa | aatgcctgga | gttccaaatg | 1320 |
| gaaatgtttg | ccacatagaa | caggaaccac | atggggtca | cagtgggcca | gaacttcagc | 1380 |
| gcactgggcg | gctatttggg | ggcttggtgc | tggacatcaa | gcggaaggcc | ccctggtact | 1440 |
| ggagcgacta | ccgagatgca | ctcagcttac | agtgtttggc | ttcctttctg | ttcctgtact | 1500 |
| gtgcctgcat | gtcacctgtc | atcacctttg | ggggactgct | tggagaagcc | actgagggac | 1560 |
| gcataagtgc | aattgaatcc | ttgtttggag | cttccatgac | tgggattgct | tattccttgt | 1620 |
| ttgcgggaca | ggctctcacc | atcctgggaa | gtactggacc | agtgcttgtg | tttgaaaaga | 1680 |
| ttttgttcaa | attctgcaaa | gactatgctc | tttcatacct | ctccctgcga | gcttgtattg | 1740 |
| gactgtggac | cgctttcctg | tgtattgtcc | ttgtggcaac | tgatgccagt | tcccttgtct | 1800 |
| gctacattac | ccgtttcact | gaagaagcat | ttgcctccct | aatttgcatt | attttcatct | 1860 |
| atgaagcaat | agaaaaactg | attcacctgg | cagagaccta | ccccatccaa | atgcacagcc | 1920 |
| agctggacca | ccttagcctc | tattactgca | ggtgtactct | gccagagaat | ccaaacaatc | 1980 |
| acaccctcca | gtactggaag | gaccacaaca | tcgtgacagc | agaagtccac | tgggctaacc | 2040 |

-continued

```
tgactgtcag tgaatgccag gagatgcatg gagagttcat gggatctgcg tgcggccatc    2100
atggacccta cactcctgat gtcctctttt ggtcctgtat tctctttttc accaccttca    2160
tcctctcaag caccttaaag acgtttaaga cgagccgtta tttcccaacc agagtacgct    2220
ccatggtgag tgactttgct gttttcctca ctatcttcac aatggtgatt attgattttt    2280
tgattggagt cccatcacca aagcttcaag ttcccagtgt gttcaagcca acaagggatg    2340
atcgcggatg gattattaat cccattggcc ccaatccctg gtggactgtg atagctgcaa    2400
ttatcccagc tcttctctgt actatcttga tattcatgga tcagcagatc acagccgtca    2460
ttattaacag gaaggaacat aagctcaaga aaggctgtgg ctaccacctg gacctactga    2520
tggtggccat catgctgggt gtctgctcca tcatgggcct gccctggttt gtagctgcaa    2580
ctgtcttgtc catcacacat gtgaacagcc tcaagctaga atctgaatgc tctgctcctg    2640
gagaacagcc caagttcctg ggcatccgag aacagagagt gacaggcctt atgatctttg    2700
tgctgatggg ctgctcagtc ttcatgacgg ctatcttaaa gtttattcca atgccagtac    2760
tctacggagt tttcctttac atgggagttt cttcactaca gggaattcag ttctttgatc    2820
gtctaaagct ctttgggatg cccgcaaagc accagccaga tttcatctac ctgcggcatg    2880
tgccgctgcg caaagtgcac ctcttcaccc tcatccagtt gacctgtctc gtcctgctct    2940
gggtcatcaa ggcatctcca gctgccattg ttttcccaat gatggttttg gccttggtct    3000
ttgtcaggaa agtcatggat ctctgtttct ctaagcgaga gctgagctgg ctagatgatc    3060
tcatgcctga aagcaaaaag aagaagttgg atgatgccaa aaagaaggcc aaggaggaag    3120
aggtcatagt ccttgcacca actgtatacc tgggggcctc aaattacaga acataggaag    3180
ggtcatgtga aaagtcagca tgtctggaat cccgagggtt atatttagga gctgggaaga    3240
ttaccccaa agatgttctc agctaagaat ggattaggga ttcttgcttc tgtctgttct    3300
taattttgg gtttgacaac cacttatttt ttcctttgtt tacaatctac tcaccaggct    3360
catacctaca atgtgaacat acagtatgcc cttattagca gattcaatgg ctcacattct    3420
ttcaaaaggt ctaatttgac aaatacataa gacccattat ttcctagaat gtttgtaata    3480
tatctaattg caaatggtgc tgtggttggc accatgcaaa gataacttgc ataggacttt    3540
ctgtcttttt tcatttccct cagcatttgg catcttgtca tctacacaat ggaccctcaa    3600
taaatggcct atatgtgcaa agaaagaatg tgtagcaaat gaaaatacca gaccaagaaa    3660
tgagtgagct gggaagtgtt tccaaataca gttagtgcct aaaatagtgt cctttgaaaa    3720
aacttttaaa agactttttt ttaggccagg cataatgggt tatccctgta attccagggc    3780
ttttgggagt tgaagctgga ggattacttg aggccagaag tttgagacta gcctaggcaa    3840
tataatgaga ccctgtctct acaaaaaaaa aaaaaaaaaa aaaaaaaaaa aaaaaaaaa     3900
aaaaaaaaaa aa                                                       3912
```

<210> SEQ ID NO 2
<211> LENGTH: 1044
<212> TYPE: PRT
<213> ORGANISM: Homo sapiens

<400> SEQUENCE: 2

Met Pro Ala Ala Gly Ser Asn Glu Pro Asp Gly Val Leu Ser Tyr Gln
1               5                   10                  15

Arg Pro Asp Glu Glu Ala Val Val Asp Gln Gly Gly Thr Ser Thr Ile
            20                  25                  30

```
Leu Asn Ile His Tyr Glu Lys Glu Leu Glu Gly His Arg Thr Leu
        35                  40                  45

Tyr Val Gly Val Arg Met Pro Leu Gly Arg Gln Ser His Arg His His
    50                  55                  60

Arg Thr His Gly Gln Lys His Arg Arg Gly Arg Gly Lys Gly Ala
65              70                  75                  80

Ser Gln Gly Glu Glu Gly Leu Glu Ala Leu Ala His Asp Thr Pro Ser
                85                  90                  95

Gln Arg Val Gln Phe Ile Leu Gly Thr Glu Glu Asp Glu His Val
                100                 105                 110

Pro His Glu Leu Phe Thr Glu Leu Asp Glu Ile Cys Met Lys Glu Gly
        115                 120                 125

Glu Asp Ala Glu Trp Lys Glu Thr Ala Arg Trp Leu Lys Phe Glu Glu
    130                 135                 140

Asp Val Glu Asp Gly Gly Glu Arg Trp Ser Lys Pro Tyr Val Ala Thr
145                 150                 155                 160

Leu Ser Leu His Ser Leu Phe Glu Leu Arg Ser Cys Leu Ile Asn Gly
                165                 170                 175

Thr Val Leu Leu Asp Met His Ala Asn Ser Ile Glu Glu Ile Ser Asp
            180                 185                 190

Leu Ile Leu Asp Gln Gln Glu Leu Ser Ser Asp Leu Asn Asp Ser Met
        195                 200                 205

Arg Val Lys Val Arg Glu Ala Leu Leu Lys Lys His His His Gln Asn
    210                 215                 220

Glu Lys Lys Arg Asn Asn Leu Ile Pro Ile Val Arg Ser Phe Ala Glu
225                 230                 235                 240

Val Gly Lys Lys Gln Ser Asp Pro His Leu Met Asp Lys His Gly Gln
                245                 250                 255

Thr Val Ser Pro Gln Ser Val Pro Thr Thr Asn Leu Glu Val Lys Asn
                260                 265                 270

Gly Val Asn Cys Glu His Ser Pro Val Asp Leu Ser Lys Val Asp Leu
            275                 280                 285

His Phe Met Lys Lys Ile Pro Thr Gly Ala Glu Ala Ser Asn Val Leu
    290                 295                 300

Val Gly Glu Val Asp Ile Leu Asp Arg Pro Ile Val Ala Phe Val Arg
305                 310                 315                 320

Leu Ser Pro Ala Val Leu Leu Ser Gly Leu Thr Glu Val Pro Ile Pro
                325                 330                 335

Thr Arg Phe Leu Phe Ile Leu Leu Gly Pro Val Gly Lys Gly Gln Gln
            340                 345                 350

Tyr His Glu Ile Gly Arg Ser Met Ala Thr Ile Met Thr Asp Glu Ile
        355                 360                 365

Phe His Asp Val Ala Tyr Lys Ala Lys Glu Arg Asp Asp Leu Leu Ala
    370                 375                 380

Gly Ile Asp Glu Phe Leu Asp Gln Val Thr Val Leu Pro Pro Gly Glu
385                 390                 395                 400

Trp Asp Pro Ser Ile Arg Ile Glu Pro Pro Lys Asn Val Pro Ser Gln
                405                 410                 415

Glu Lys Arg Lys Met Pro Gly Val Pro Asn Gly Asn Val Cys His Ile
            420                 425                 430

Glu Gln Glu Pro His Gly Gly His Ser Gly Pro Glu Leu Gln Arg Thr
    435                 440                 445

Gly Arg Leu Phe Gly Gly Leu Val Leu Asp Ile Lys Arg Lys Ala Pro
```

-continued

```
                450                 455                 460
Trp Tyr Trp Ser Asp Tyr Arg Asp Ala Leu Ser Leu Gln Cys Leu Ala
465                 470                 475                 480

Ser Phe Leu Phe Leu Tyr Cys Ala Cys Met Ser Pro Val Ile Thr Phe
                485                 490                 495

Gly Gly Leu Leu Gly Glu Ala Thr Glu Gly Arg Ile Ser Ala Ile Glu
                500                 505                 510

Ser Leu Phe Gly Ala Ser Met Thr Gly Ile Ala Tyr Ser Leu Phe Ala
                515                 520                 525

Gly Gln Ala Leu Thr Ile Leu Gly Ser Thr Gly Pro Val Leu Val Phe
530                 535                 540

Glu Lys Ile Leu Phe Lys Phe Cys Lys Asp Tyr Ala Leu Ser Tyr Leu
545                 550                 555                 560

Ser Leu Arg Ala Cys Ile Gly Leu Trp Thr Ala Phe Leu Cys Ile Val
                565                 570                 575

Leu Val Ala Thr Asp Ala Ser Ser Leu Val Cys Tyr Ile Thr Arg Phe
                580                 585                 590

Thr Glu Glu Ala Phe Ala Ser Leu Ile Cys Ile Ile Phe Ile Tyr Glu
                595                 600                 605

Ala Ile Glu Lys Leu Ile His Leu Ala Glu Thr Tyr Pro Ile Gln Met
610                 615                 620

His Ser Gln Leu Asp His Leu Ser Leu Tyr Tyr Cys Arg Cys Thr Leu
625                 630                 635                 640

Pro Glu Asn Pro Asn Asn His Thr Leu Gln Tyr Trp Lys Asp His Asn
                645                 650                 655

Ile Val Thr Ala Glu Val His Trp Ala Asn Leu Thr Val Ser Glu Cys
                660                 665                 670

Gln Glu Met His Gly Glu Phe Met Gly Ser Ala Cys Gly His His Gly
                675                 680                 685

Pro Tyr Thr Pro Asp Val Leu Phe Trp Ser Cys Ile Leu Phe Phe Thr
                690                 695                 700

Thr Phe Ile Leu Ser Ser Thr Leu Lys Thr Phe Lys Thr Ser Arg Tyr
705                 710                 715                 720

Phe Pro Thr Arg Val Arg Ser Met Val Ser Asp Phe Ala Val Phe Leu
                725                 730                 735

Thr Ile Phe Thr Met Val Ile Asp Phe Leu Ile Gly Val Pro Ser
                740                 745                 750

Pro Lys Leu Gln Val Pro Ser Val Phe Lys Pro Thr Arg Asp Asp Arg
                755                 760                 765

Gly Trp Ile Ile Asn Pro Ile Gly Pro Asn Pro Trp Trp Thr Val Ile
                770                 775                 780

Ala Ala Ile Ile Pro Ala Leu Leu Cys Thr Ile Leu Ile Phe Met Asp
785                 790                 795                 800

Gln Gln Ile Thr Ala Val Ile Ile Asn Arg Lys Glu His Lys Leu Lys
                805                 810                 815

Lys Gly Cys Gly Tyr His Leu Asp Leu Met Val Ala Ile Met Leu
                820                 825                 830

Gly Val Cys Ser Ile Met Gly Leu Pro Trp Phe Val Ala Ala Thr Val
                835                 840                 845

Leu Ser Ile Thr His Val Asn Ser Leu Lys Leu Glu Ser Glu Cys Ser
                850                 855                 860

Ala Pro Gly Glu Gln Pro Lys Phe Leu Gly Ile Arg Glu Gln Arg Val
865                 870                 875                 880
```

```
Thr Gly Leu Met Ile Phe Val Leu Met Gly Cys Ser Val Phe Met Thr
             885                 890                 895
Ala Ile Leu Lys Phe Ile Pro Met Pro Val Leu Tyr Gly Val Phe Leu
         900                 905                 910
Tyr Met Gly Val Ser Ser Leu Gln Gly Ile Gln Phe Phe Asp Arg Leu
         915                 920                 925
Lys Leu Phe Gly Met Pro Ala Lys His Gln Pro Asp Phe Ile Tyr Leu
         930                 935                 940
Arg His Val Pro Leu Arg Lys Val His Leu Phe Thr Leu Ile Gln Leu
945                 950                 955                 960
Thr Cys Leu Val Leu Leu Trp Val Ile Lys Ala Ser Pro Ala Ala Ile
             965                 970                 975
Val Phe Pro Met Met Val Leu Ala Leu Val Phe Val Arg Lys Val Met
             980                 985                 990
Asp Leu Cys Phe Ser Lys Arg Glu Leu Ser Trp Leu Asp Asp Leu Met
             995                 1000                1005
Pro Glu Ser Lys Lys Lys Lys Leu Asp Asp Ala Lys Lys Lys Ala Lys
         1010                1015                1020
Glu Glu Glu Val Ile Val Leu Ala Pro Thr Val Tyr Leu Gly Ala Ser
1025                1030                1035                1040
Asn Tyr Arg Thr
```

<210> SEQ ID NO 3
<211> LENGTH: 2880
<212> TYPE: DNA
<213> ORGANISM: Homo sapiens

<400> SEQUENCE: 3

```
acagaagtgc caatcccaac aagattttg tttatcttat tgggtccagt agggaaaggt      60
cagcagtacc atgagattgg cagatccatg gccaccatca tgacagatga gattttcat    120
gacgtagcat ataaggcaaa agagcgagat gatctcctgg cggggattga tgagttccta    180
gaccaggtga cggtgctccc tccaggagag tgggatccct ccattagaat tgagccaccc    240
aaaaatgtcc cttcccagga gaaaggaaa atgcctggag ttccaaatgg aaatgttgc     300
cacatagaac aggaaccaca tgggggtcac agtgggccag aacttcagcg cactgggcgg    360
ctatttgggg gcttggtgct ggacatcaag cggaaggccc cctggtactg gagcgactac    420
cgagatgcac tcagcttaca gtgtttggct cctttctgt tcctgtactg tgcctgcatg     480
tcacctgtca tcacctttgg gggactgctt ggagaagcca ctgagggacg cataagtgca    540
attgaatcct tgtttggagc ttccatgact gggattgctt attccttgtt tgcgggacag    600
gctctcacca tcctgggaag tactggacca gtgcttgtgt ttgaaaagat tttgttcaaa    660
ttctgcaaag actatgctct ttcatacctc tccctgcgag cttgtattgg actgtggacc    720
gctttcctgt gtattgtcct tgtggcaact gatgccagtt cccttgtctg ctacattacc    780
cgtttcactg aagaagcatt tgcctcccta atttgcatta ttttcatcta tgaagcaata    840
gaaaaactga ttcacctggc agagacctac cccatccaca tgcacagcca gctggaccac    900
cttagcctct attactgcag gtgtactctg ccagagaatc aaacaatca cccctccag     960
tactggaagg accacaacat cgtgacagca gaagtccact gggctaacct gactgtcagt   1020
gaatgccagg agatgcatgg agagttcatg ggatctgcgt gcggccatca tggaccctac   1080
actcctgatg tcctcttttg gtcctgtatt ctcttttca ccaccttcat cctctcaagc    1140
```

-continued

```
accttaaaga cgtttaagac gagccgttat ttcccaacca gagtacgctc catggtgagt   1200
gactttgctg ttttcctcac tatcttcaca atggtgatta ttgattttt gattggagtc    1260 ccatcaccaa agcttcaagt tcccagtgtg ttcaagccaa caagggatga tcgcggatgg   1320
attattaatc ccattggccc caatccctgg tggactgtga tagctgcaat tatcccagct   1380
cttctctgta ctatcttgat attcatggat cagcagatca cagccgtcat tattaacagg   1440
aaggaacata agctcaagaa aggctgtggc taccacctgg acctactgat ggtggccatc   1500
atgctgggtg tctgctccat catgggcctg ccctggtttg tagctgcaac tgtcttgtcc   1560
atcacacatg tgaacagcct caagctagaa tctgaatgct ctgctcctgg agaacagccc   1620
aagttcctgg gcatccgaga acagagagtg acaggcctta tgatcttgt gctgatgggc    1680 tgctcagtct tcatgacggc tatcttaaag tttattccaa tgccagtact ctacggagtt   1740
ttcctttaca tgggagtttc ttcactacag gaattcagt tctttgatcg tctaaagctc     1800
tttgggatgc ccgcaaagca ccagccagat ttcatctacc tgcggcatgt gccgctgcgc   1860
aaagtgcacc tcttcaccct catccagttg acctgtctcg tcctgctctg ggtcatcaag   1920
gcatctccag ctgccattgt tttcccaatg atggttttgg ccttggtctt tgtcaggaaa   1980
gtcatggatc tctgtttctc taagcgagag ctgagctggc tagatgatct catgcctgaa   2040
agcaaaaaga agaagttgga tgatgccaaa agaaggcca aggaggaaga ggtcatagtc      2100
cttgcaccaa ctgtatacct gggggcctca aattacagaa cataggaagg gtcatgtgaa   2160
aagtcagcat gtctggaatc ccgagggtta tatttaggag ctgggaagat taccccccaaa  2220 gatgttctca gctaagaatg gattaggat tcttgcttct gtctgttctt aatttttggg     2280
tttgacaacc acttatttt tcctttgttt acaatctact caccaggctc atacctacaa     2340
tgtgaacata cagtatgccc ttattagcag attcaatggc tcacattctt tcaaaaggtc    2400
taatttgaca aatacataag acccattatt tcctagaatg tttgtaatat atctaattgc    2460
aaatggtgct gtggttggca ccatgcaaag ataacttgca taggactttc tgtcttttt     2520 catttccctc agcatttggc atcttgtcat ctacacaatg daccctcaat aaatggccta   2580
tatgtgcaaa gaaagaatgt gtagcaaatg aaaataccag accaagaaat gagtgagctg    2640
ggaagtgttt ccaaatacag ttagtgccta aaatagtgtc ctttgaaaaa acttttaaaa    2700 gactttttt taggccaggc ataatgggtt atccctgtaa ttccagggct tttgggagtt     2760
gaagctggag gattacttga ggccagaagt ttgagactag cctaggcaat ataatgagac    2820
cctgtctcta caaaaaaaaa aaaaaaaaaa aaaaaaaaaa aaaaaaaaa aaaaaaaaa      2880
```

<210> SEQ ID NO 4
<211> LENGTH: 714
<212> TYPE: PRT
<213> ORGANISM: Homo sapiens

<400> SEQUENCE: 4

```
Thr Glu Val Pro Ile Pro Thr Arg Phe Leu Phe Ile Leu Leu Gly Pro
  1               5                  10                  15

Val Gly Lys Gly Gln Gln Tyr His Glu Ile Gly Arg Ser Met Ala Thr
             20                  25                  30

Ile Met Thr Asp Glu Ile Phe His Asp Val Ala Tyr Lys Ala Lys Glu
         35                  40                  45

Arg Asp Asp Leu Leu Ala Gly Ile Asp Glu Phe Leu Asp Gln Val Thr
     50                  55                  60

Val Leu Pro Pro Gly Glu Trp Asp Pro Ser Ile Arg Ile Glu Pro Pro
```

-continued

```
                65                  70                  75                  80
Lys Asn Val Pro Ser Gln Glu Lys Arg Lys Met Pro Gly Val Pro Asn
                    85                  90                  95
Gly Asn Val Cys His Ile Glu Gln Glu Pro His Gly Gly His Ser Gly
                    100                 105                 110
Pro Glu Leu Gln Arg Thr Gly Arg Leu Phe Gly Gly Leu Val Leu Asp
                    115                 120                 125
Ile Lys Arg Lys Ala Pro Trp Tyr Trp Ser Asp Tyr Arg Asp Ala Leu
            130                 135                 140
Ser Leu Gln Cys Leu Ala Ser Phe Leu Phe Leu Tyr Cys Ala Cys Met
    145                 150                 155                 160
Ser Pro Val Ile Thr Phe Gly Gly Leu Leu Gly Glu Ala Thr Glu Gly
                    165                 170                 175
Arg Ile Ser Ala Ile Glu Ser Leu Phe Gly Ala Ser Met Thr Gly Ile
                    180                 185                 190
Ala Tyr Ser Leu Phe Ala Gly Gln Ala Leu Thr Ile Leu Gly Ser Thr
                    195                 200                 205
Gly Pro Val Leu Val Phe Glu Lys Ile Leu Phe Lys Phe Cys Lys Asp
            210                 215                 220
Tyr Ala Leu Ser Tyr Leu Ser Leu Arg Ala Cys Ile Gly Leu Trp Thr
225                 230                 235                 240
Ala Phe Leu Cys Ile Val Leu Val Ala Thr Asp Ala Ser Ser Leu Val
                    245                 250                 255
Cys Tyr Ile Thr Arg Phe Thr Glu Glu Ala Phe Ala Ser Leu Ile Cys
                    260                 265                 270
Ile Ile Phe Ile Tyr Glu Ala Ile Glu Lys Leu Ile His Leu Ala Glu
                    275                 280                 285
Thr Tyr Pro Ile His Met His Ser Gln Leu Asp His Leu Ser Leu Tyr
                    290                 295                 300
Tyr Cys Arg Cys Thr Leu Pro Glu Asn Pro Asn Asn His Thr Leu Gln
305                 310                 315                 320
Tyr Trp Lys Asp His Asn Ile Val Thr Ala Glu Val His Trp Ala Asn
                    325                 330                 335
Leu Thr Val Ser Glu Cys Gln Glu Met His Gly Glu Phe Met Gly Ser
                    340                 345                 350
Ala Cys Gly His His Gly Pro Tyr Thr Pro Asp Val Leu Phe Trp Ser
                    355                 360                 365
Cys Ile Leu Phe Phe Thr Thr Phe Ile Leu Ser Ser Thr Leu Lys Thr
                    370                 375                 380
Phe Lys Thr Ser Arg Tyr Phe Pro Thr Arg Val Arg Ser Met Val Ser
385                 390                 395                 400
Asp Phe Ala Val Phe Leu Thr Ile Phe Thr Met Val Ile Ile Asp Phe
                    405                 410                 415
Leu Ile Gly Val Pro Ser Pro Lys Leu Gln Val Pro Ser Val Phe Lys
                    420                 425                 430
Pro Thr Arg Asp Asp Arg Gly Trp Ile Ile Asn Pro Ile Gly Pro Asn
                    435                 440                 445
Pro Trp Trp Thr Val Ile Ala Ala Ile Pro Ala Leu Leu Cys Thr
                    450                 455                 460
Ile Leu Ile Phe Met Asp Gln Gln Ile Thr Ala Val Ile Ile Asn Arg
465                 470                 475                 480
Lys Glu His Lys Leu Lys Lys Gly Cys Gly Tyr His Leu Asp Leu Leu
                    485                 490                 495
```

```
Met Val Ala Ile Met Leu Gly Val Cys Ser Ile Met Gly Leu Pro Trp
            500                 505                 510

Phe Val Ala Ala Thr Val Leu Ser Ile Thr His Val Asn Ser Leu Lys
            515                 520                 525

Leu Glu Ser Glu Cys Ser Ala Pro Gly Glu Gln Pro Lys Phe Leu Gly
            530                 535                 540

Ile Arg Glu Gln Arg Val Thr Gly Leu Met Ile Phe Val Leu Met Gly
545                 550                 555                 560

Cys Ser Val Phe Met Thr Ala Ile Leu Lys Phe Ile Pro Met Pro Val
                565                 570                 575

Leu Tyr Gly Val Phe Leu Tyr Met Gly Val Ser Ser Leu Gln Gly Ile
            580                 585                 590

Gln Phe Phe Asp Arg Leu Lys Leu Phe Gly Met Pro Ala Lys His Gln
            595                 600                 605

Pro Asp Phe Ile Tyr Leu Arg His Val Pro Leu Arg Lys Val His Leu
            610                 615                 620

Phe Thr Leu Ile Gln Leu Thr Cys Leu Val Leu Leu Trp Val Ile Lys
625                 630                 635                 640

Ala Ser Pro Ala Ala Ile Val Phe Pro Met Met Val Leu Ala Leu Val
                645                 650                 655

Phe Val Arg Lys Val Met Asp Leu Cys Phe Ser Lys Arg Glu Leu Ser
                660                 665                 670

Trp Leu Asp Asp Leu Met Pro Glu Ser Lys Lys Lys Leu Asp Asp
            675                 680                 685

Ala Lys Lys Lys Ala Lys Glu Glu Val Ile Val Leu Ala Pro Thr
            690                 695                 700

Val Tyr Leu Gly Ala Ser Asn Tyr Arg Thr
705                 710

<210> SEQ ID NO 5
<211> LENGTH: 385
<212> TYPE: DNA
<213> ORGANISM: Homo sapiens

<400> SEQUENCE: 5
acagaagtgc caatcccaac aagatttttg tttatcttat tgggtccagt agggaaaggt    60
cagcagtacc atgagattgg cagatccatg gccaccatca tgacagatga gattttcat    120 gacgtnncat ataaggcaaa agagcgagat gatctcctgg cggggattga tgagttccta    180
gaccaggtga cggtgctccc tccaggagag tgggatccct ccattagaat tgagccaccc    240
aaaaatgtcc cttcccagga gaaaggaaa atgcctggaa gttccaaatg gaaatgtttg    300
ccacatagaa caggaaccac nggggtcac atgggccaga acttcancgc angggcggc    360 tatttggggg nttggtggct ggnac                                         385

<210> SEQ ID NO 6
<211> LENGTH: 90
<212> TYPE: PRT
<213> ORGANISM: Homo sapiens

<400> SEQUENCE: 6

Thr Glu Val Pro Val Pro Thr Arg Phe Leu Phe Ile Leu Leu Gly Pro
  1               5                  10                  15

Lys Gly Lys Ala Lys Ser Tyr His Glu Ile Gly Arg Ser Ile Ala Thr
             20                  25                  30
```

```
Leu Met Ser Asp Glu Val Phe His Asp Ile Ala Tyr Lys Ala Lys Asn
            35                  40                  45

Arg Glu Asp Leu Ile Ala Gly Ile Asp Glu Phe Leu Asp Glu Val Ile
        50                  55                  60

Val Leu Pro Leu Gly Glu Trp Asp Pro Thr Ile Arg Ile Glu Pro Pro
65                  70                  75                  80

Lys Ser Leu Pro Ser Ser Asp Lys Arg Lys
                85                  90

<210> SEQ ID NO 7
<211> LENGTH: 3842
<212> TYPE: DNA
<213> ORGANISM: Homo sapiens

<400> SEQUENCE: 7
agaccagatg aagaagctgt ggtggatcag ggtgggacca gtacaattct caacattcac     60
tatgaaaaag aagagctgga agaccttctg cttctttcca ggtcacagaa ctctgtatgt    120
gggagttcgg atgccgcttg ccggcagag ccatcggcat caccgcactc atggccagaa    180
gcaccggaga cgagggcggg gcaaaggagc cagccagggg gaggaaggcc tggaagccct    240
ggcccacgac acaccatctc agcgtgttca gttcattctt ggcaccgagg aagatgaaga    300
gcatgtgcct catgagctgt ttacagagct ggatgagatc tgtatgaaag agggagaaga    360
tgctgagtgg aaggaaacag ccaggtggct gaagtttgaa gaagatgttg aagatgggg    420 agaacgctgg agcaagcctt atgtggcaac ccttcattg cacagcctgt ttgagctaag    480
gagctgcctt attaatggaa cagtcctcct ggatatgcat gcaaatagca tagaagaaat    540
ttcagacctg atcctggatc agcaagaact gtccagtgac ctgaatgaca gcatgagggt    600
taaagtgcgg gaagcccttc tcaaaaagca tcatcatcag aatgaaaaga agagaaacaa    660
cctcattccc attgttcgct ccttttgctga ggttggcaag aagcagtctg atcctcattt    720
gatggataaa catggtcaaa ccgtgtctcc tcagtctgtt ccaactacaa atcttgaagt    780
aaaaaatgga gtgaattgtg aacatagtcc tgtggattta agcaaggtag accttcattt    840
catgaaaaaa attcctactg gggccgaggc ctccaatgtc ctggttggag aggtggatat    900
tttggaccgt cccattgttg cctttgtgag gctgtctcca gctgttcttc tctcaggcct    960
aacagaagtg ccaatcccaa caagattttt gtttatctta ttgggtccag tagggaaagg   1020
tcagcagtac catgagattg gcagatccat ggccaccatc atgacagatg agatttttca   1080
tgacgtagca tataaggcaa aagagcgaga tgatctcctg gcggggattg atgagttcct   1140
agaccaggtg acggtgctcc ctccaggaga gtgggatccc tccattagaa ttgagccacc   1200
caaaaatgtc ccttcccagg agaaaggaa atgcctgga gttccaaatg gaaatgtttg   1260
ccacatagaa caggaaccac atgggggtca cagtgggcca gaacttcagc gcactgggcg   1320
gctatttggg ggcttggtgc tggacatcaa gcggaaggcc ccctggtact ggagcgacta   1380
ccgagatgca ctcagcttac agtgtttggc ttccttttctg ttcctgtact gtgcctgcat   1440
gtcacctgtc atcacctttg ggggactgct tggagaagcc actgagggac gcataagtgc   1500
aattgaatcc ttgtttggag cttccatgac tgggattgct tattccttgt ttgcgggaca   1560
ggctctcacc atcctgggaa gtactggacc agtgcttgtg tttgaaaaga ttttgttcaa   1620
attctgcaaa gactatgctc tttcataacct ctccctgcga gcttgtattg gactgtggac   1680
cgctttcctg tgtattgtcc ttgtggcaac tgatgccagt tcccttgtct gctacattac   1740
ccgtttcact gaagaagcat ttgcctccct aatttgcatt atttttcatct atgaagcaat   1800
```

| | |
|---|---|
| agaaaaactg attcacctgg cagagaccta ccccatccaa atgcacagcc agctggacca | 1860 |
| ccttagcctc tattactgca ggtgtactct gccagagaat ccaaacaatc acaccctcca | 1920 |
| gtactggaag gaccacaaca tcgtgacagc agaagtccac tgggctaacc tgactgtcag | 1980 |
| tgaatgccag gagatgcatg gagagttcat gggatctgcg tgcggccatc atggaccta | 2040 |
| cactcctgat gtcctctttt ggtcctgtat tctcttttc accaccttca tcctctcaag | 2100 |
| caccttaaag acgtttaaga cgagccgtta tttcccaacc agagtacgct ccatggtgag | 2160 |
| tgactttgct gttttcctca ctatcttcac aatggtgatt attgattttt tgattggagt | 2220 |
| cccatcacca aagcttcaag ttcccagtgt gttcaagcca acaagggatg atcgcggatg | 2280 |
| gattattaat cccattggcc ccaatccctg gtggactgtg atagctgcaa ttatcccagc | 2340 |
| tcttctctgt actatcttga tattcatgga tcagcagatc acagccgtca ttattaacag | 2400 |
| gaaggaacat aagctcaaga aggctgtgg ctaccacctg gacctactga tggtggccat | 2460 |
| catgctgggt gtctgctcca tcatgggcct gccctggttt gtagctgcaa ctgtcttgtc | 2520 |
| catcacacat gtgaacagcc tcaagctaga atctgaatgc tctgctcctg agaacagcc | 2580 |
| caagttcctg ggcatccgag aacagagagt gacaggcctt atgatctttg tgctgatggg | 2640 |
| ctgctcagtc ttcatgacgg ctatcttaaa gtttattcca atgccagtac tctacggagt | 2700 |
| tttcctttac atgggagttt cttcactaca gggaattcag ttctttgatc gtctaaagct | 2760 |
| ctttgggatg cccgcaaagc accagccaga tttcatctac ctgcggcatg tgccgctgcg | 2820 |
| caaagtgcac ctcttcaccc tcatccagtt gacctgtctc gtcctgctct gggtcatcaa | 2880 |
| ggcatctcca gctgccattg tttcccaat gatggttttg gccttggtct ttgtcaggaa | 2940 |
| agtcatggat ctctgtttct ctaagcgaga gctgagctgg ctagatgatc tcatgcctga | 3000 |
| aagcaaaaag aagaagttgg atgatgccaa aaagaaggcc aaggaggaag aggtcatagt | 3060 |
| ccttgcacca actgtatacc tgggggcctc aaattacaga acataggaag ggtcatgtga | 3120 |
| aaagtcagca tgtctggaat cccgagggtt atatttagga gctgggaaga ttaccccaa | 3180 |
| agatgttctc agctaagaat ggattaggga ttcttgcttc tgtctgttct taattttgg | 3240 |
| gtttgacaac cacttatttt ttcctttgtt tacaatctac tcaccaggct catacctaca | 3300 |
| atgtgaacat acagtatgcc cttattagca gattcaatgg ctcacattct ttcaaaaggt | 3360 |
| ctaatttgac aaatacataa gacccattat ttcctagaat gtttgtaata tatctaattg | 3420 |
| caaatggtgc tgtggttggc accatgcaaa gataacttgc ataggacttt ctgtctttt | 3480 |
| tcatttccct cagcatttgg catcttgtca tctacacaat ggaccctcaa taaatggcct | 3540 |
| atatgtgcaa agaaagaatg tgtagcaaat gaaaatacca gaccaagaaa tgagtgagct | 3600 |
| gggaagtgtt tccaaataca gttagtgcct aaaatagtgt cctttgaaaa aacttttaaa | 3660 |
| agactttttt ttaggccagg cataatgggt tatccctgta attccaggc ttttgggagt | 3720 |
| tgaagctgga ggattacttg aggccagaag tttgagacta gcctaggcaa tataatgaga | 3780 |
| ccctgtctct acaaaaaaaa aaaaaaaaa aaaaaaaaa aaaaaaaaa aaaaaaaaa | 3840 |
| aa | 3842 |

<210> SEQ ID NO 8
<211> LENGTH: 1032
<212> TYPE: PRT
<213> ORGANISM: Homo sapiens

<400> SEQUENCE: 8

-continued

```
Met Lys Lys Leu Trp Trp Ile Arg Val Gly Pro Val Gln Phe Ser Thr
 1               5                  10                 15

Phe Thr Met Lys Lys Lys Ser Trp Lys Thr Phe Cys Phe Phe Pro Gly
            20                  25                 30

His Arg Thr Leu Tyr Val Gly Val Arg Met Pro Leu Gly Arg Gln Ser
            35                  40                 45

His Arg His His Arg Thr His Gly Gln Lys His Arg Arg Arg Gly Arg
        50                  55                 60

Gly Lys Gly Ala Ser Gln Gly Glu Gly Leu Glu Ala Leu Ala His
 65                 70                  75                 80

Asp Thr Pro Ser Gln Arg Val Gln Phe Ile Leu Gly Thr Glu Glu Asp
                85                  90                 95

Glu Glu His Val Pro His Glu Leu Phe Thr Glu Leu Asp Glu Ile Cys
            100                 105                110

Met Lys Glu Gly Glu Asp Ala Glu Trp Lys Glu Thr Ala Arg Trp Leu
            115                 120                125

Lys Phe Glu Glu Asp Val Glu Asp Gly Gly Glu Arg Trp Ser Lys Pro
130                 135                 140

Tyr Val Ala Thr Leu Ser Leu His Ser Leu Phe Glu Leu Arg Ser Cys
145                 150                 155                160

Leu Ile Asn Gly Thr Val Leu Leu Asp Met His Ala Asn Ser Ile Glu
                165                 170                175

Glu Ile Ser Asp Leu Ile Leu Asp Gln Gln Glu Leu Ser Ser Asp Leu
                180                 185                190

Asn Asp Ser Met Arg Val Lys Val Arg Glu Ala Leu Leu Lys Lys His
                195                 200                205

His His Gln Asn Glu Lys Lys Arg Asn Asn Leu Ile Pro Ile Val Arg
        210                 215                 220

Ser Phe Ala Glu Val Gly Lys Lys Gln Ser Asp Pro His Leu Met Asp
225                 230                 235                240

Lys His Gly Gln Thr Val Ser Pro Gln Ser Val Pro Thr Thr Asn Leu
                245                 250                255

Glu Val Lys Asn Gly Val Asn Cys Glu His Ser Pro Val Asp Leu Ser
                260                 265                270

Lys Val Asp Leu His Phe Met Lys Lys Ile Pro Thr Gly Ala Glu Ala
            275                 280                 285

Ser Asn Val Leu Val Gly Glu Val Asp Ile Leu Asp Arg Pro Ile Val
            290                 295                 300

Ala Phe Val Arg Leu Ser Pro Ala Val Leu Leu Ser Gly Leu Thr Glu
305                 310                 315                320

Val Pro Ile Pro Thr Arg Phe Leu Phe Ile Leu Leu Gly Pro Val Gly
                325                 330                335

Lys Gly Gln Gln Tyr His Glu Ile Gly Arg Ser Met Ala Thr Ile Met
            340                 345                 350

Thr Asp Glu Ile Phe His Asp Val Ala Tyr Lys Ala Lys Glu Arg Asp
            355                 360                 365

Asp Leu Leu Ala Gly Ile Asp Glu Phe Leu Asp Gln Val Thr Val Leu
        370                 375                 380

Pro Pro Gly Glu Trp Asp Pro Ser Ile Arg Ile Glu Pro Pro Lys Asn
385                 390                 395                400

Val Pro Ser Gln Glu Lys Arg Lys Met Pro Gly Val Pro Asn Gly Asn
                405                 410                415

Val Cys His Ile Glu Gln Glu Pro His Gly Gly His Ser Gly Pro Glu
```

-continued

```
                420             425             430
Leu Gln Arg Thr Gly Arg Leu Phe Gly Gly Leu Val Leu Asp Ile Lys
            435             440             445
Arg Lys Ala Pro Trp Tyr Trp Ser Asp Tyr Arg Asp Ala Leu Ser Leu
    450             455             460
Gln Cys Leu Ala Ser Phe Leu Phe Leu Tyr Cys Ala Cys Met Ser Pro
465             470             475             480
Val Ile Thr Phe Gly Gly Leu Leu Gly Glu Ala Thr Glu Gly Arg Ile
            485             490             495
Ser Ala Ile Glu Ser Leu Phe Gly Ala Ser Met Thr Gly Ile Ala Tyr
                500             505             510
Ser Leu Phe Ala Gly Gln Ala Leu Thr Ile Leu Gly Ser Thr Gly Pro
            515             520             525
Val Leu Val Phe Glu Lys Ile Leu Phe Lys Phe Cys Lys Asp Tyr Ala
    530             535             540
Leu Ser Tyr Leu Ser Leu Arg Ala Cys Ile Gly Leu Trp Thr Ala Phe
545             550             555             560
Leu Cys Ile Val Leu Val Ala Thr Asp Ala Ser Ser Leu Val Cys Tyr
            565             570             575
Ile Thr Arg Phe Thr Glu Glu Ala Phe Ala Ser Leu Ile Cys Ile Ile
                580             585             590
Phe Ile Tyr Glu Ala Ile Glu Lys Leu Ile His Leu Ala Glu Thr Tyr
            595             600             605
Pro Ile Gln Met His Ser Gln Leu Asp His Leu Ser Leu Tyr Tyr Cys
    610             615             620
Arg Cys Thr Leu Pro Glu Asn Pro Asn His Thr Leu Gln Tyr Trp
625             630             635             640
Lys Asp His Asn Ile Val Thr Ala Glu Val His Trp Ala Asn Leu Thr
            645             650             655
Val Ser Glu Cys Gln Glu Met His Gly Glu Phe Met Gly Ser Ala Cys
                660             665             670
Gly His His Gly Pro Tyr Thr Pro Asp Val Leu Phe Trp Ser Cys Ile
            675             680             685
Leu Phe Phe Thr Thr Phe Ile Leu Ser Ser Thr Leu Lys Thr Phe Lys
            690             695             700
Thr Ser Arg Tyr Phe Pro Thr Arg Val Arg Ser Met Val Ser Asp Phe
705             710             715             720
Ala Val Phe Leu Thr Ile Phe Thr Met Val Ile Asp Phe Leu Ile
            725             730             735
Gly Val Pro Ser Pro Lys Leu Gln Val Pro Ser Val Phe Lys Pro Thr
            740             745             750
Arg Asp Asp Arg Gly Trp Ile Ile Asn Pro Ile Gly Pro Asn Pro Trp
            755             760             765
Trp Thr Val Ile Ala Ala Ile Pro Ala Leu Leu Cys Thr Ile Leu
    770             775             780
Ile Phe Met Asp Gln Gln Ile Thr Ala Val Ile Ile Asn Arg Lys Glu
785             790             795             800
His Lys Leu Lys Lys Gly Cys Gly Tyr His Leu Asp Leu Leu Met Val
            805             810             815
Ala Ile Met Leu Gly Val Cys Ser Ile Met Gly Leu Pro Trp Phe Val
            820             825             830
Ala Ala Thr Val Leu Ser Ile Thr His Val Asn Ser Leu Lys Leu Glu
            835             840             845
```

Ser Glu Cys Ser Ala Pro Gly Glu Gln Pro Lys Phe Leu Gly Ile Arg
850                 855                 860

Glu Gln Arg Val Thr Gly Leu Met Ile Phe Val Leu Met Gly Cys Ser
865                 870                 875                 880

Val Phe Met Thr Ala Ile Leu Lys Phe Ile Pro Met Pro Val Leu Tyr
                885                 890                 895

Gly Val Phe Leu Tyr Met Gly Val Ser Ser Leu Gln Gly Ile Gln Phe
                900                 905                 910

Phe Asp Arg Leu Lys Leu Phe Gly Met Pro Ala Lys His Gln Pro Asp
                915                 920                 925

Phe Ile Tyr Leu Arg His Val Pro Leu Arg Lys Val His Leu Phe Thr
                930                 935                 940

Leu Ile Gln Leu Thr Cys Leu Val Leu Leu Trp Val Ile Lys Ala Ser
945                 950                 955                 960

Pro Ala Ala Ile Val Phe Pro Met Met Val Leu Ala Leu Val Phe Val
                965                 970                 975

Arg Lys Val Met Asp Leu Cys Phe Ser Lys Arg Glu Leu Ser Trp Leu
                980                 985                 990

Asp Asp Leu Met Pro Glu Ser Lys Lys Lys Leu Asp Asp Ala Lys
                995                 1000                1005

Lys Lys Ala Lys Glu Glu Val Ile Val Leu Ala Pro Thr Val Tyr
        1010                1015                1020

Leu Gly Ala Ser Asn Tyr Arg Thr
1025                1030

<210> SEQ ID NO 9
<211> LENGTH: 475
<212> TYPE: DNA
<213> ORGANISM: Homo sapiens

<400> SEQUENCE: 9
ggacgaggtt tgcgggacag gctctcacca tcctgggaag tactggacca gtgcttgttt      60
ttgaaaagat tttnttcaaa ttctgcaaag actatgctct tcatacctc tccctgcgag      120 cttgtattgg actgtggacc gctttcctgt gtattgtcct tgtggcaact gatgccagtt     180
cccttgtctg ctacattacc cgtttcactg aagaagcatt tgcctcccta atttgcatta     240
ttttcatcta tgaagcaata gaaaaactga ttcacctggc agagacctac cccatccaca     300
tgcacagcca gctggaccac cttagcctct attactgcag gtgtactctg ccagagaatc     360
caaacantca caccctccag tactggaagg accacaacat cgtgacagca gaagtccact     420
gggttaacnt gantgttcat gtaagtttgg gngttgccag ttgtcntagg cntgt          475

<210> SEQ ID NO 10
<211> LENGTH: 119
<212> TYPE: PRT
<213> ORGANISM: Homo sapiens

<400> SEQUENCE: 10

Phe Gly Gly Gln Pro Leu Thr Ile Leu Ser Ser Thr Gly Pro Val Leu
 1               5                  10                  15

Val Phe Glu Arg Leu Leu Phe Asn Phe Ser Lys Asp Asn Asp Phe Asp
                20                  25                  30

Tyr Leu Glu Phe Arg Leu Trp Ile Gly Leu Trp Ser Ala Phe Gln Cys
            35                  40                  45

Leu Ile Leu Val Ala Thr Asp Ala Ser Phe Leu Val Lys Tyr Phe Thr

-continued

```
              50                  55                  60
Arg Phe Thr Glu Glu Gly Phe Ser Ser Leu Ile Ser Phe Ile Phe Ile
 65                  70                  75                  80

Tyr Asp Ala Phe Lys Lys Met Ile Lys Leu Ala Asp Tyr Tyr Pro Ile
                 85                  90                  95

Asn Ser His Phe Lys Val Asp Tyr Ile Thr Gln Tyr Ser Cys Ala Cys
            100                 105                 110

Phe Pro Pro Glu Pro Ala Asn
        115
``` what is claimed is:

1. An isolated polynucleotide comprising a nucleotide sequence encoding the polypeptide of SEQ ID NO:2.

2. The isolated polynucleotide of claim 1 consisting of a nucleotide sequence encoding the polypeptide of SEQ ID NO:2.

3. An isolated polynucleotide comprising the polynucleotide of SEQ ID NO:1.

4. The isolated polynucleotide of claim 3 that is the polynucleotide of SEQ ID NO:1.

5. An isolated polynucleotide obtainable by screening an appropriate library under stringent hybridization conditions with a labeled probe having the sequence of SEQ ID NO:1, wherein said isolated polynucleotide encodes a sodium bicarbonate transporter.

6. An expression system comprising a polynucleotide capable of encoding a polypeptide comprising the amino acid sequence of SEQ ID NO:2 when said expression system is present in a compatible host cell.

7. A process for producing a recombinant host cell comprising transforming or transfecting a cell with the expression system of claim 6 such that the host cell, under appropriate culture conditions, produces a polypeptide having the amino acid sequence of SEQ ID NO:2.

8. A recombinant host cell produced by the process of claim 7.

9. A process for producing a polypeptide comprising culturing the host cell of claim 8 under conditions sufficient for the production of said polypeptide and recovering said polypeptide from the culture.

10. An isolated polynucleotide comprising a nucleotide sequence encoding the polypeptide of SEQ ID NO:8.

11. The isolated polynucleotide of claim 10 consisting of a nucleotide sequence encoding the polypeptide of SEQ ID NO:8.

12. An isolated polynucleotide comprising the polynucleotide of SEQ ID NO:7.

13. The isolated polynucleotide of claim 12 that is the polynucleotide of SEQ ID NO:7.

14. An isolated polynucleotide obtainable by screening an appropriate library under stringent hybridization conditions with a labeled probe having the sequence of SEQ ID NO:7, wherein said isolated polynucleotide encodes a sodium bicarbonate transporter.

15. An expression system comprising a polynucleotide capable of encoding a polypeptide comprising the amino acid sequence of SEQ ID NO:8 when said expression system is present in a compatible host cell.

16. A process for producing a recombinant host cell comprising transforming or transfecting a cell with the expression system of claim 15 such that the host cell, under appropriate culture conditions, produces a polypeptide having the amino acid sequence of SEQ ID NO:8.

17. A recombinant host cell produced by the process of claim 16.

18. A process for producing a polypeptide comprising culturing the host cell of claim 17 under conditions sufficient for the production of said polypeptide and recovering said polypeptide from the culture.

19. An isolated polynucleotide which is fully complementary to the isolated polynucleotide encoding SEQ ID NO:2.

20. The isolated polynucleotide of claim 19 which is fully complementary to the polynucleotide sequence of SEQ ID NO:1.

* * * * *